(12) United States Patent
Dorney

(10) Patent No.: US 7,046,412 B2
(45) Date of Patent: May 16, 2006

(54) SCANNING OPTICAL DELAY LINE USING A REFLECTIVE ELEMENT ARRANGED TO ROTATE

(76) Inventor: Timothy D. Dorney, 5102 Stillbrook Dr., Houston, TX (US) 77035-3131

( * ) Notice: Subject to any disclaimer, the term of this patent is extended or adjusted under 35 U.S.C. 154(b) by 88 days.

(21) Appl. No.: 10/457,678

(22) Filed: Jun. 9, 2003

(65) Prior Publication Data

US 2004/0246550 A1    Dec. 9, 2004

(51) Int. Cl.
*G02B 26/08* (2006.01)
(52) U.S. Cl. ...................... 359/226; 359/203
(58) Field of Classification Search ............... 359/201, 359/202, 15, 17, 18, 566, 572, 364–366, 359/726–736, 876
See application file for complete search history.

(56) References Cited

U.S. PATENT DOCUMENTS

| | | |
|---|---|---|
| 3,776,637 A | 12/1973 | Hecht |
| 4,002,830 A | 1/1977 | Brown et al. ............... 358/293 |
| 5,007,721 A | 4/1991 | Morris et al. |
| 5,146,368 A | 9/1992 | Fink ............................ 359/861 |
| 5,151,812 A * | 9/1992 | Watson ........................ 359/201 |
| 5,220,463 A | 6/1993 | Edelstein et al. ........... 359/857 |
| 5,274,435 A * | 12/1993 | Hettrick ....................... 356/328 |
| 5,387,969 A | 2/1995 | Marantette |
| 5,598,292 A * | 1/1997 | Yoshikawa et al. ......... 359/216 |
| 5,751,419 A | 5/1998 | Takahashi et al. .......... 356/321 |
| 6,147,799 A | 11/2000 | MacDonald ................ 359/380 |
| 6,191,862 B1 | 2/2001 | Swanson et al. |
| 6,407,872 B1 | 6/2002 | Lai et al. .................... 359/833 |

FOREIGN PATENT DOCUMENTS

JP        58240025       7/1985

OTHER PUBLICATIONS

"Rotary Mirror Array for High-Speed Optical Coherence Tomography", Authors: Nan Guang Chen and Quing Zhu, As published in: Optics Letters, Optical Society of America, Apr. 15, 2002, vol. 27, No. 8 (3 pages).
"400-Hz Mechanical Scanning Optical Delay Line", Authors: K.F. Kwong, D. Yankelvich, K.C. Chu, J.P. Heritage, and A. Dienes, as published in Optics Letters, vol. 18, No. 7, Apr. 1, 1993.
"High-Speed Phase-and Group-Delay Scanning With a Grating-Based Phase Control Delay Line", Authors: G.J. Tearney, B.E. Bouma, and J.G. Fujimoto, as published in Optics Letters, vol. 22, No. 23, Dec. 1, 1997.
A Rapid Scanning Autocorrelation Scheme for Continuous Monitoring of Picosecond Laser Pulses, Authors: Zafer A. Yasa and Nabil M. Amer, as published in Optics Communications, vol. 36, No. 5, Mar. 1, 1981.

* cited by examiner

*Primary Examiner*—James Phan
(74) *Attorney, Agent, or Firm*—Timothy D. Dorney

(57) ABSTRACT

A method and apparatus delays an optical input using a scanning optical delay line. The scanning optical delay line includes an optical input and an optical output. A reflective element is arranged to rotate about an axis such that the reflective element maintains a constant incidence angle between the optical input and the reflective element for at least a portion of a rotation of the reflective element.

16 Claims, 10 Drawing Sheets

SCANNING OPTICAL DELAY LINE USING A REFLECTIVE ELEMENT ARRANGED TO ROTATE

BACKGROUND OF INVENTION

A pump/probe experiment is a commonly used method for performing time-resolved measurements on ultra-fast time scales. Two pulses (i.e., a pump pulse and a probe pulse) are typically used to investigate a system. The pump pulse is used to excite a response in the system. The probe pulse, which is delayed with respect to the pump pulse, is used to gather information about the excited system at a particular time delay. By varying the time delay between the pump pulse and the probe pulse, information about the temporal response of the system to the pump pulse may be obtained.

A time delay between the pump pulse and the probe pulse may be achieved by reflecting one of the pulse trains off a slowly moving retro-reflector mounted on a motorized translation stage. The signal is obtained by chopping one beam and using a lock-in amplifier (LIA) referenced to a chopping frequency to minimize source noise in the passband of the LIA. Using a slowly moving retro-reflector is usually referred to as a slow scan technique.

Another technique is rapid, repetitive scanning and signal averaging. Many fast scans can be taken and averaged together. Signal fluctuations are averaged or filtered to reduce noise. Depending on the number of signals that are averaged, several orders of magnitude reduction in noise may be achieved.

Typical rapid, repetitive scanning apparatus may have a scan rate of several tens of Hertz and may have scan ranges of approximately 150 picoseconds or less. Rapid, repetitive scanning apparatus may be mounted on a motorized translation stage to extend the scan ranges. Signals may be concatenated to create a single signal with a scan range longer than the scan range provided solely by the rapid, repetitive scanning apparatus. A typical design or control tradeoff in the rapid, repetitive scanning apparatus is the scan range versus the scan rate. Typically, as the scan range decreases, the scan rate may increase, and vice versa. Also, linearity of the delay may be a design or control tradeoff of the rapid, repetitive scanning apparatus.

FIG. 1 shows a diagram of a typical rapid, repetitive scanning apparatus (100). A retro-reflecting mirror (104) moves in movement (133) to a secondary position (108). The movement (133) is repeated so that the retro-reflecting mirror (104) translates between positions.

An optical input (101), or optical input beam, impinges on the retro-reflecting mirror (104). An incidence angle, $\theta$, between the optical input (101) and a line normal to the retro-reflecting mirror (104) may be measured when the optical input (101), or optical input beam, impinges on the retro-reflecting mirror (104). An optical output (103) maintains the same incidence angle, $\theta$, on an opposite side of the line normal to the retro-reflecting mirror (104). The optical output (103) impinges the retro-reflecting mirror (104) at a different location than the optical input (101), which results in an optical output (105).

The optical input (101) and the optical output (105) are parallel to each other. As the retro-reflecting mirror (104) sweeps forward and backward, the optical input (101) and the optical output (105) continue to be parallel to each other. For example, as the retro-reflecting mirror (104) moves to the secondary position (108), the optical input (101) continues along optical path (107). The optical input (101) impinges on the retro-reflecting mirror (104) at the secondary position (108) and is reflected along optical path (109). Furthermore, the optical input (101) is reflected from optical path (109) to optical path (111) to form the optical output (105). Accordingly, as the retro-reflecting mirror (104) sweeps forward and backward, an optical delay is changed depending on the distance an optical beam travels.

Ideally, an optical delay has a linear temporal delay. In other words, as the retro-reflecting mirror (104) sweeps forward and backward, the retro-reflecting mirror (104) moves at a constant velocity. If the movement (133) has a constant velocity, the temporal delay of the optical beam is linear. In the typical rapid, repetitive scanning apparatus (100), the retro-reflecting mirror (104) sweeps forward, stops, sweeps backward, stops, and repeats the forward movement. The retro-reflecting mirror (104) has a mass that must be stopped, then accelerated. Accordingly, the retro-reflecting mirror (104) may only move with a constant velocity during a portion of the forward and backward movement (133).

Furthermore, time is required for the retro-reflecting mirror (104) to sweep forward and backward. As the scan range (i.e., a distance traveled by the retro-reflecting mirror (104)) increases, the scan rate (i.e., the time required to travel the distance) decreases, and vice versa.

SUMMARY OF INVENTION

According to one aspect of one or more embodiments of the present invention, the present invention relates to an apparatus comprising a first reflective element arranged to rotate about a first axis where the first reflective element is configured to maintain a constant incidence angle between a first optical input and the first reflective element for at least a portion of a rotation of the first reflective element and where the first reflective element is configured to maintain a constant incidence angle between the first reflective element and a first optical output for at least the portion of the rotation of the first reflective element.

According to one aspect of one or more embodiments of the present invention, the present invention relates to a method for delaying an optical beam comprising rotating a first reflective element; propagating a first optical input beam to the first reflective element where the first reflective element is configured to maintain a constant incidence angle between the first optical input beam and the first reflective element for at least a portion of a rotation of the first reflective element; and propagating a first optical output beam responsive to the first optical input beam incident on the first reflective element.

According to one aspect of one or more embodiments of the present invention, the present invention relates to an apparatus comprising means for reflecting an optical beam where the means for reflecting is configured to maintain a constant incidence angle between an input optical beam and the means for reflecting for at least a portion of a rotation of the means for reflecting; and means for rotating the means for reflecting.

Other aspects and advantages of the invention will be apparent from the following description and the appended claims.

DETAILED DESCRIPTION

Embodiments of the present invention relate to a scanning optical delay line formed by rotation of a reflective element. The reflective element is designed to provide a constant incidence angle between an optical input and the reflective element for at least a portion of a rotation of the reflective element. The reflective element may be used in combination with one or more stationary reflective elements. Furthermore, the reflective element may be used with at least one additional reflective element that rotates. The at least one additional reflective element may have a shape that is a mirror image of a shape of the original reflective element that rotates.

One of ordinary skill in the art will understand that a reflective element may include, but is not limited to, a front surface mirror, a rear surface mirror, a mirror, a grating, and a wavelength selective reflective element. One or more similar or different types of reflective elements may be combined in a system. For purposes of illustration and discussion, a front surface reflective element is used. Accordingly, use of the term "reflective element," and more generally the term "mirror," along with the exemplary drawings that illustrate a front surface reflective element, should not be construed to limit the present invention solely to a front surface mirror. The figures may not be drawn to scale or a consistent perspective; however, one of ordinary skill in the art, having benefit of this disclosure, will understand and will be aided by the figures.

One of ordinary skill in the art will understand that a means for propagating an optical input, an optical output, and/or an optical beam may include, but is not limited to, a front surface mirror, a rear surface mirror, a mirror, a grating, a wavelength selective reflective element, a lens or lenses, beam splitter, polarizer, fiber optics, optical amplifier, optical multiplexer, and optical demultiplexer. Further, the means may include associated hardware to support, hold, and/or align the elements listed above.

Figure 1:
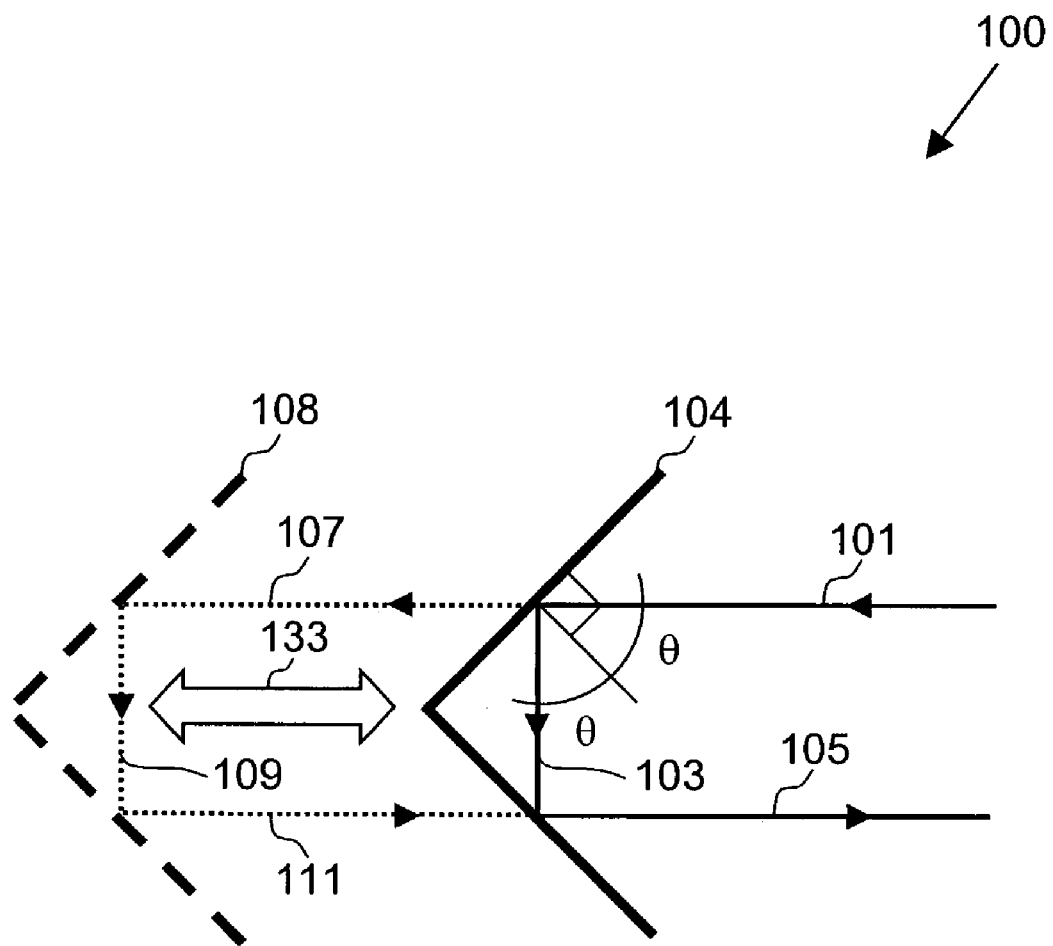
FIG. 1 shows a diagram of a typical rapid, repetitive optical scanning apparatus.
Figure 2:
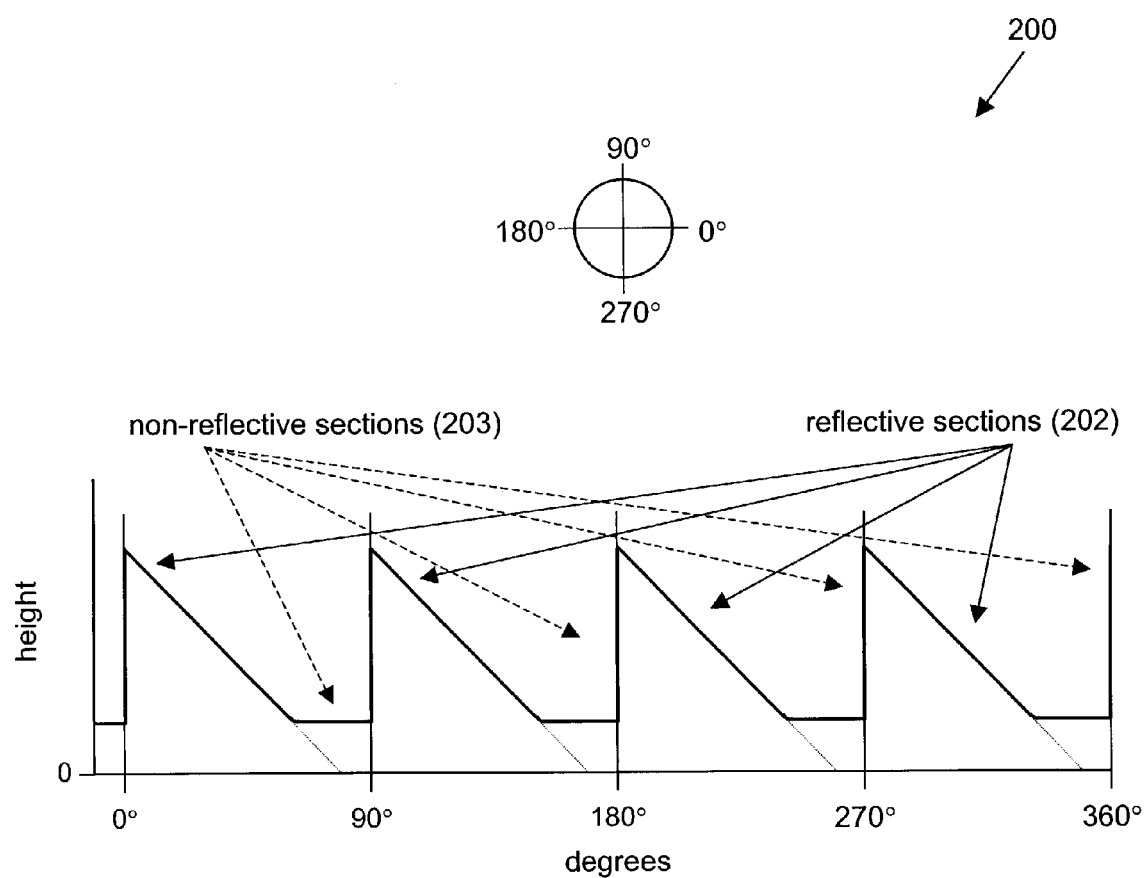
FIG. 2 shows a graph of a two-dimensional pattern to be applied to concentric rings centered about an origin in accordance with an embodiment of the present invention.

FIG. 2 shows a graph of an exemplary two-dimensional pattern (200) to be applied to concentric rings centered about an origin in accordance with an embodiment of the present invention. The two-dimensional pattern (200) includes a plurality of linear reflective sections (202) and non-reflective sections (203). One of ordinary skill in the art, having benefit of this disclosure, will understand that a two-dimensional pattern may have a single linear reflective section. Also, a two-dimensional pattern may have a plurality of linear reflective sections.

The two-dimensional pattern (200) includes a plurality of linear reflective sections (202). The two-dimensional pattern (200) is a surface pattern applied to concentric rings centered about an origin as a surface of a reflective element designed to rotate. Because the two-dimensional pattern (200) includes linear reflective sections (202), a reflective element that rotates and has the shape shown in two-dimensional pattern (200) maintains a linear temporal delay. In other words, a reflective element arranged to rotate about an axis having the shape shown in the two-dimensional pattern (200) also maintains a constant incidence angle (i.e., an angle between an optical beam and a line normal to a surface of a reflective element at the point where the optical beam impinges on the reflective element) between an optical input and the reflective element for at least a portion of a rotation of the reflective element. Also, the reflective element maintains a constant incidence angle between the optical output and the reflective element for at least the portion of the rotation of the reflective element.

Equations may define a desired arrangement for the linear reflective sections (202). For example, the following linear equations are provided:

$$0° \leq \theta \leq 56° \quad y = -(42/90°)\,\theta + 45, \quad (1)$$

$$90° \leq \theta \leq 146° \quad y = -42/90°\,(\theta - 90°) + 45, \quad (2)$$

$$180° \leq \theta \leq 236° \quad y = -42/90°\,(\theta - 180°) + 45, \quad (3)$$

$$270° \leq \theta \leq 326° \quad y = -42/90°\,(\theta - 270°) + 45, \quad (4)$$

where $\theta$ is a position along an arc of constant radius about an origin, and y is a desired height of a two-dimensional pattern at the position $\theta$. Sections not defined by Equations 1–4 may be non-reflective sections; therefore, the non-reflective sections may have various shapes.

As indicated in this example, the two-dimensional pattern (200) is mapped in a counter-clockwise direction. However, those skilled in the art will understand that, in one or more other embodiments, a pattern may be mapped in a clockwise direction.

If the desired two-dimensional pattern (200) is mapped onto a plurality of concentric rings centered about an origin, a resulting reflective element provides a linear ramp along an arc of constant radius. In other words, for any given distance from the origin, a linear ramp occurs as a path is traveled along the constant radius. In this example, four linear ramp sections, or linear reflective sections (202), are formed along the entire 360° path for the reflective element. Part of the entire 360° path is required to be reflective while the remaining portion is not required to be reflective. However, those skilled in the art will understand that, in one or more other embodiments, a pattern may require that the entire 360° path is reflective.

One of ordinary skill in the art, having benefit of the present invention, will understand that a number of linear regions is a design or control tradeoff. For a reflective element with a fixed diameter, an increase in the number of linear regions generally corresponds to a decrease in an amount of delay for each linear region assuming each linear region is similar. Conversely, a decrease in the number of linear regions generally corresponds to an increase in an amount of delay for each linear region assuming each linear region is similar.

Figure 3:
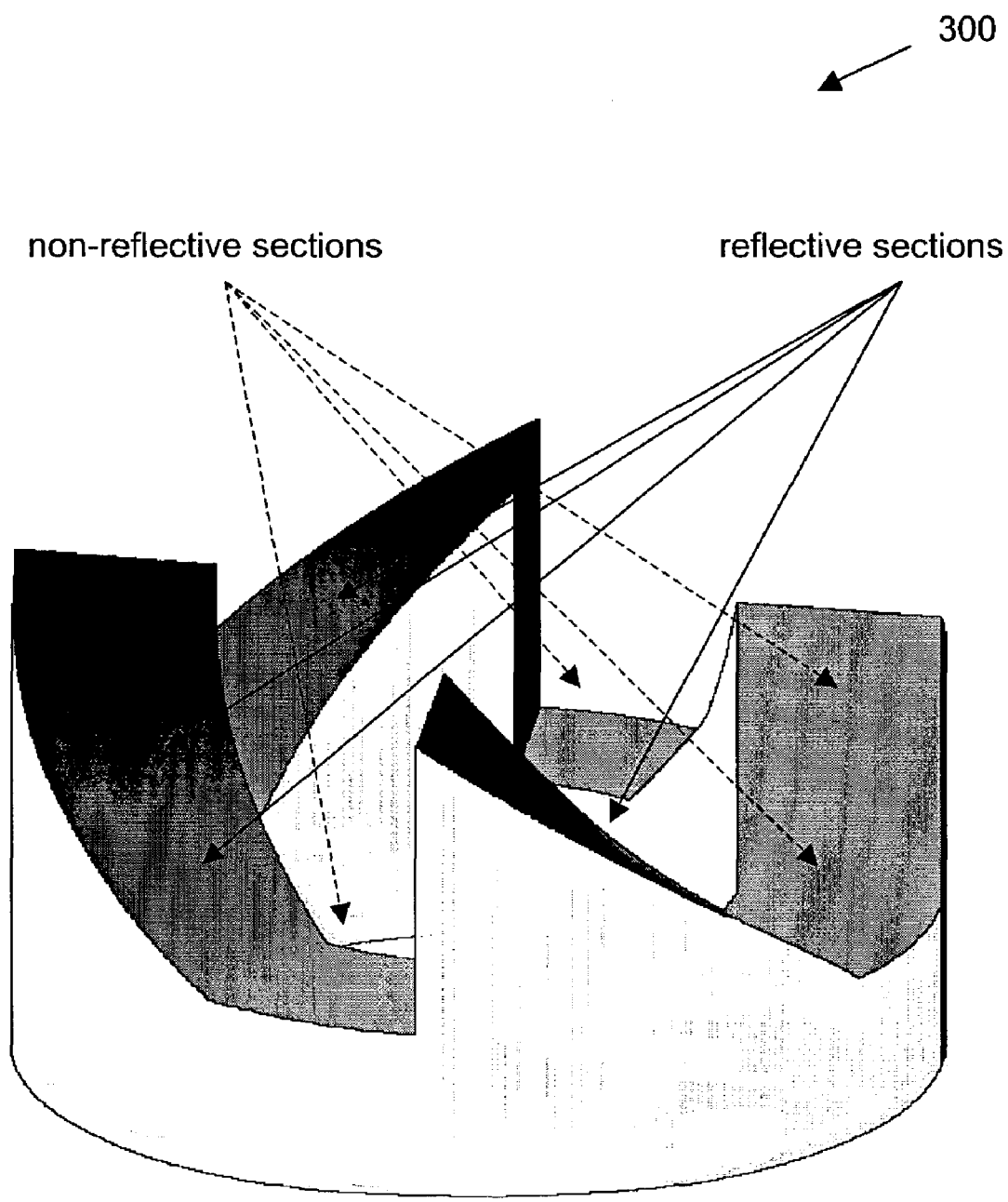
FIG. 3 shows a side view diagram of a reflective element with a two-dimensional pattern applied to concentric rings centered about an origin in accordance with an embodiment of the present invention.

FIG. 3 shows a side view diagram of an exemplary reflective element (300) with a two-dimensional pattern applied to concentric rings centered about an origin in accordance with an embodiment of the present invention. The two-dimensional pattern (200) shown in FIG. 2 has been applied to a plurality of concentric rings centered about the origin of the reflective element (300). The reflective element (300) includes a plurality of linear reflective sections and non-reflective sections. A linear ramp occurs along an arc of constant radius for any of the reflective sections. Furthermore, any radial line from the origin of the reflective element (300) along any of the reflective sections will have a constant height. In other words, a linear temporal delay is provided for an optical input that impinges on any arc of constant radius for any of the reflective sections.

Figure 4:
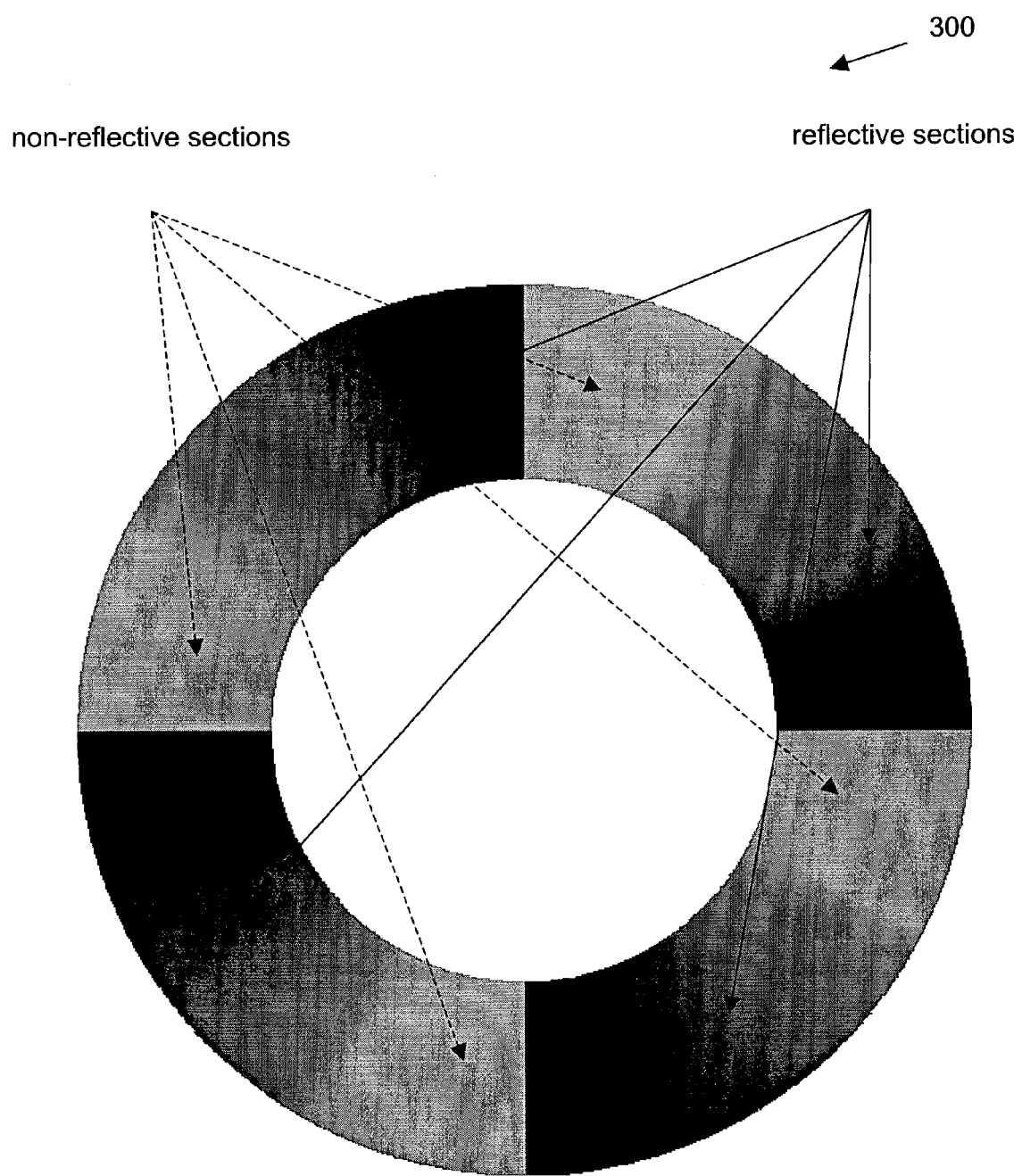
FIG. 4 shows a top view diagram of a reflective element with a two-dimensional pattern applied to concentric rings centered about an origin in accordance with an embodiment of the present invention.

FIG. 4 shows a top view diagram of an exemplary reflective element (300) with a two-dimensional pattern applied to concentric rings centered about an origin in accordance with an embodiment of the present invention. The two-dimensional pattern (200) shown in FIG. 2 has been applied to a plurality of concentric rings centered about the origin of the reflective element (300). The reflective element (300) includes a plurality of linear reflective sections and non-reflective sections. A linear ramp occurs along an arc of constant radius for any of the reflective sections. Furthermore, any radial line from the origin of the reflective element (300) along any of the reflective sections will have a constant height. In other words, a linear temporal delay is provided for an optical input that impinges on any arc of constant radius for any of the reflective sections.

Figure 5:
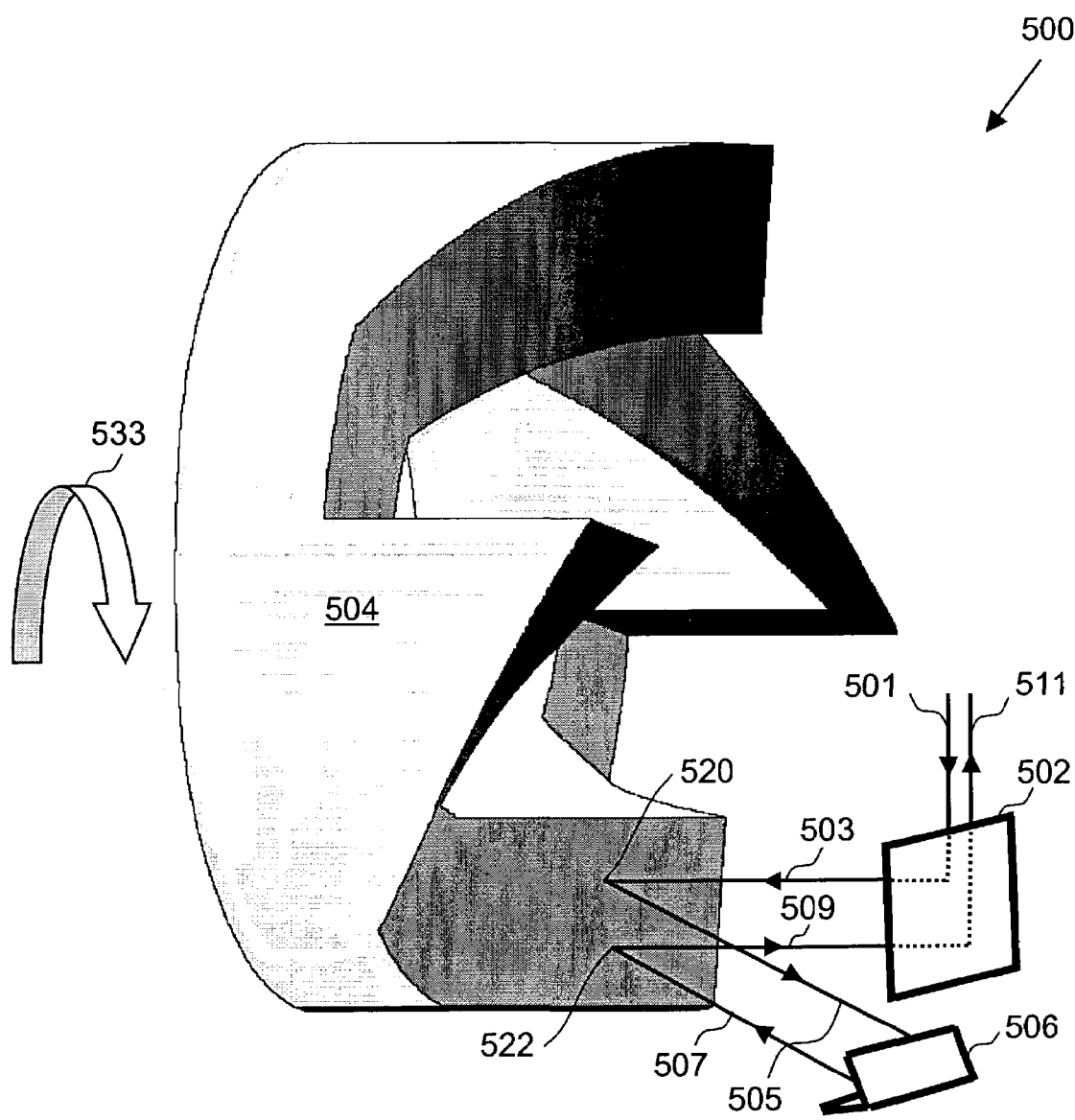
FIG. 5 shows a diagram of an optical beam path using a reflective element arranged to rotate with a two-dimensional pattern applied to concentric rings centered about an origin in accordance with an embodiment of the present invention.

FIG. 5 shows a diagram of an exemplary optical beam path (500) using a reflective element (504) arranged to rotate with a two-dimensional pattern applied to concentric rings centered about an origin in accordance with an embodiment of the present invention. An optical input (501) impinges onto a steering mirror (502) that steers the optical input (501) onto the reflective element (504) along optical path (503). The reflective element (504) may be similar to the reflective elements (300 shown in FIG. 3 and in FIG. 4) discussed above.

An optical output (505) results from the optical input (501) reflecting off of the reflective element (504). The reflective element (504) rotates about an axis indicated by a rotation direction (533). As the reflective element (504) rotates, a constant incidence angle is maintained between the reflective element (504) and the optical input (501) along optical path (503) for at least a portion of the rotation of the reflective element (504). Also, as the reflective element (504) rotates, a constant incidence angle is maintained between the reflective element (504) and the optical output (505) for at least a portion of the rotation of the reflective element (504). Although the constant incidence angle is maintained for at least a portion of the rotation of the reflective element (504), a point (520) at which the optical input (501) along optical path (503) impinges on the reflective element (504) is not the same.

As the reflective element (504) rotates and the point (520) changes, the optical output (505) follows parallel paths. Accordingly, the optical output (505) impinges at different points on a stationary retro-reflector (506) where the different points follow a straight line. For example, with respect to FIG. 5, when the point (520) is near the right side of a reflective section of the reflective element (504), the optical output (505) impinges near the right side of the stationary retro-reflector (506). When the point (520) is near the left side of the reflective section of the reflective element (504), the optical output (505) impinges near the left side of the stationary retro-reflector (506).

In one or more embodiments, the stationary retro-reflector (506) may be a two sided (i.e., roof top or periscope) front surface reflecting, retro-reflector. Preferably, the stationary retro-reflector (506) includes two flat reflecting surfaces, typically at ninety degrees to each other. Accordingly, the optical output (505) is retro-reflected along a parallel optical path to produce an optical output (507). Because the optical output (505) moves along the stationary retro-reflector (506) in parallel paths as the reflective element (504) rotates, the optical output (507) also moves along a parallel path with respect to optical output (505). The optical output (507) may impinge on the reflective section of the reflective element (504) at a point (522) that is on the same radial line from an origin about which the concentric rings are centered as the point (520).

Because optical outputs (505, 507) are parallel and the constant incidence angle is maintained between the reflective element (504) and the optical outputs (505, 507) for at least a portion of the rotation of the reflective element (504), an optical path (509) is parallel to the optical path (503). Optical output (511) results from an optical beam along optical path (509) impinging on the steering mirror (502). Accordingly, the optical input (501) and the optical output (511) are parallel. Furthermore, the optical path (509) is a stationary optical path (i.e., does not move) with respect to optical path (503).

One of ordinary skill in the art will understand that, in one or more embodiments, the steering mirror (502) may not be used. Accordingly, the optical input (501) may have a path similar to optical path (503). Furthermore, optical output (511) may have a path similar to optical path (509).

Conversely, in one or more embodiments, an additional steering mirror may be used with steering mirror (502). Accordingly, the optical input (501) may impinge on steering mirror (502) and the optical output (511) along optical path (509) may impinge on the additional steering mirror. The optical output (511) along optical path (509) may have a stationary, but non-parallel optical path, with respect to the optical input (501) along optical path (503). The non-parallel optical path may result from the optical output (507) impinging on the reflective section of the reflective element (504) at a point that is not on the same radial line from an origin about which the concentric rings are centered as the point (520).

Figure 6:
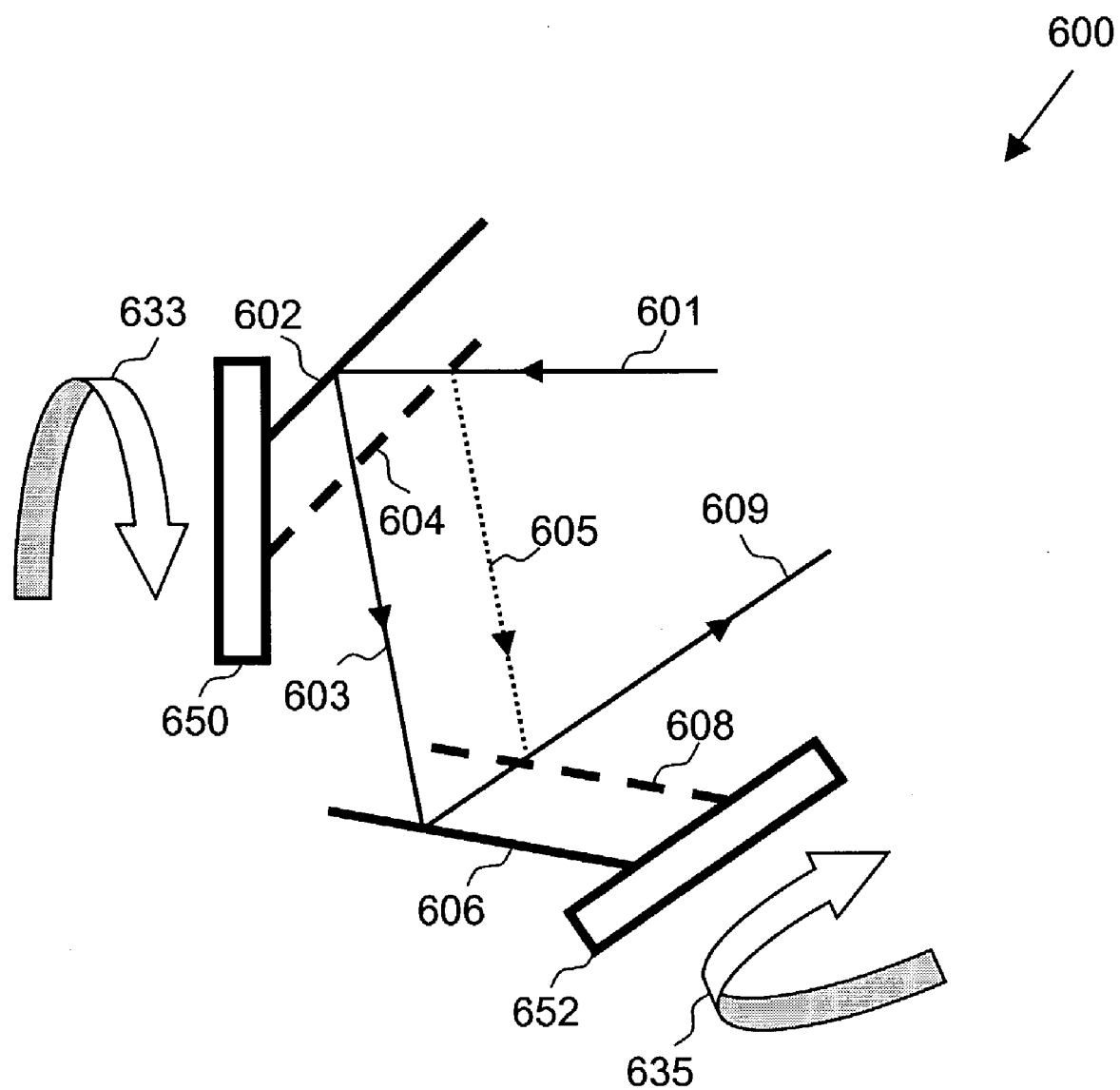
FIG. 6 shows a diagram of an optical beam path using two reflective elements arranged to rotate with a two-dimensional pattern applied to concentric rings centered about an origin in accordance with an embodiment of the present invention.

FIG. 6 shows a diagram of an exemplary optical beam path (600) using two reflective elements arranged to rotate with a two-dimensional pattern applied to concentric rings centered about an origin in accordance with an embodiment of the present invention. An optical input (601) impinges onto a reflective section (602) of a first reflective element (650) that results in an optical output (603). The optical output (603) impinges onto a reflective section (606) of a second reflective element (652) that results in an optical output (609). The first reflective element (650) and the second reflective element (652) may be similar to the reflective elements (300 shown in FIG. 3 and in FIG. 4) discussed above.

As the first reflective element (650) rotates in a rotation direction (633) and the second reflective element (652) rotates in a rotation direction (635), the reflective section (602) of the first reflective element (650) and the reflective section (606) of the second reflective element (652) move. Accordingly, the reflective section (602) of the first reflective element (650) may move to a second position (604). Also, the reflective section (606) of the second reflective element (652) may move to a second position (608). The optical input (601) impinges onto the reflective section (602) of the first reflective element (650) at the second position (604) that results in an optical output (605). The optical output (605) impinges onto the reflective section (606) of the second reflective element (652) at the second position (608) that results in the optical output (609).

The optical output (603) has an optical path length that is longer than an optical path length for optical output (605). Accordingly, different temporal delays may be generated. Furthermore, by using reflective elements arranged to rotate with linear reflective sections, a linear temporal delay may be obtained.

The optical input (601) and the optical output (609) have a stationary path while impinging on reflective sections (602, 606) of the first reflective element (650) and the second reflective element (652), respectively. One of ordinary skill in the art will understand that the optical input (601) and the optical output (609) may be made parallel using one or more steering mirrors.

Figure 7:
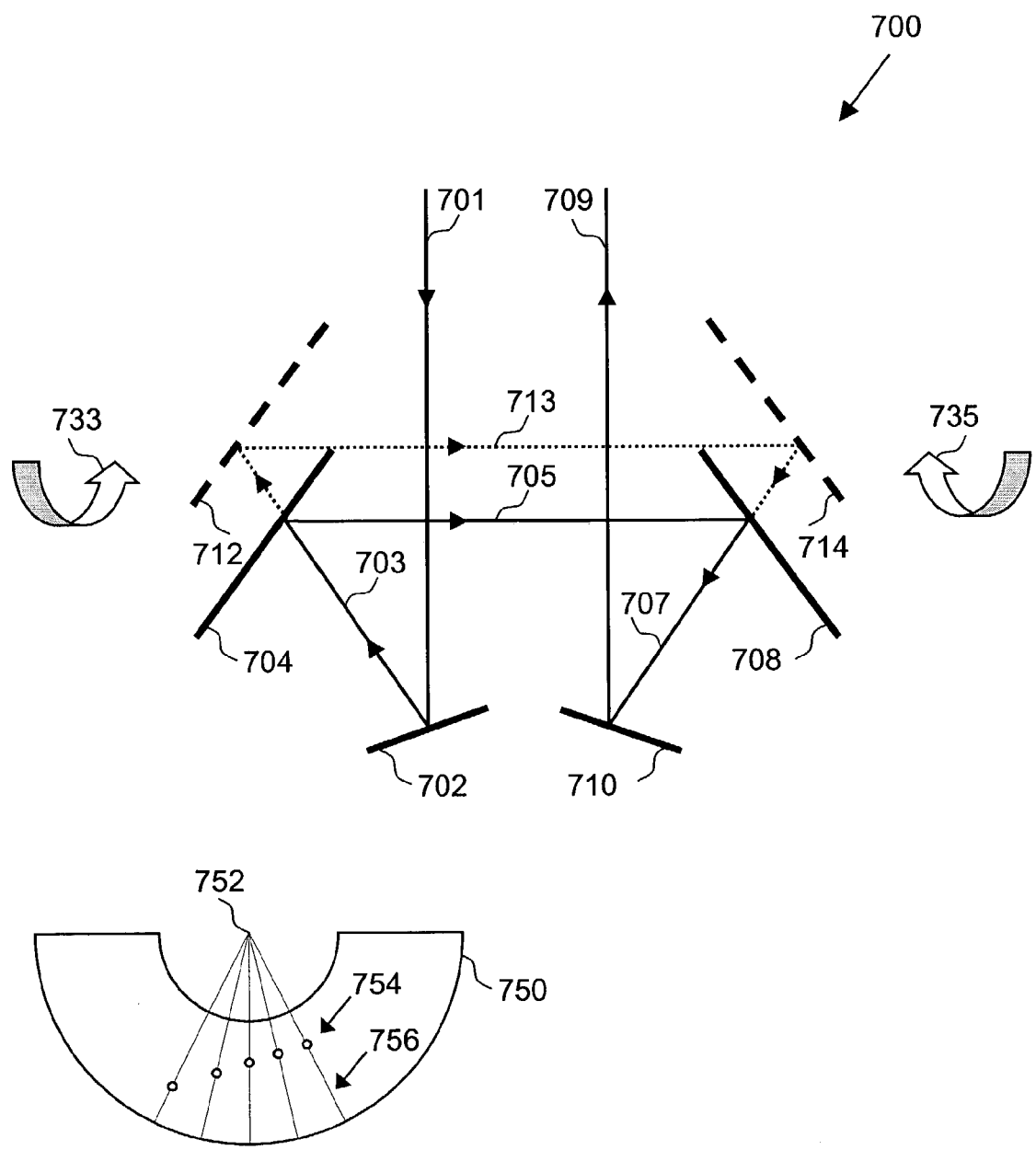
FIG. 7 shows a diagram of an optical beam path using two reflective elements arranged to rotate with a two-dimensional pattern applied to concentric rings centered about an origin in accordance with an embodiment of the present invention.

FIG. 7 shows a diagram of an exemplary optical beam path (700) using two reflective elements arranged to rotate with a two-dimensional pattern applied to concentric rings centered about an origin in accordance with an embodiment of the present invention. An optical input (701) impinges onto a steering mirror (702) that steers the optical input (701) along optical path (703) onto a reflective section (704) of a first reflective element. The first reflective element may be similar to the reflective elements (300 shown in FIG. 3 and in FIG. 4) discussed above. The optical input (701) along optical path (703) impinging on the reflective section (704) of the first reflective element results in an optical output (705).

The optical output (705) impinges onto a reflective section (708) of a second reflective element. The second reflective element may be a mirror image of the first reflective element. The optical output (705) impinging on the reflective section (708) of the second reflective element results in an optical output (707). The optical output (707) impinges onto a steering mirror (710) that may steer the optical output (709) parallel to the optical input (701).

As the first reflective element rotates in a rotation direction (733) and the second reflective element rotates in a rotation direction (735), the reflective section (704) of the first reflective element and the reflective section (708) of the second reflective element move. Accordingly, the reflective section (704) of the first reflective element may move to a second position (712). Also, the reflective section (708) of the second reflective element may move to a second position (714). The optical input (701) along optical path (703) impinges onto the reflective section (704) of the first reflective element at the second position (712) that results in an optical output (713). The optical output (713) impinges onto the reflective section (708) of the second reflective element at the second position (714) that results in the optical output (707).

The optical output (713) has an optical path length that is longer than an optical path length for optical output (705). Accordingly, different temporal delays may be generated. Also, by using reflective elements arranged to rotate with linear reflective sections, a linear temporal delay may be obtained. Furthermore, the first reflective element and the second reflective element may both rotate about the same axis or axial location.

An optical input may not necessary be arranged to impinge on a reflective section along an arc of constant radius. For example, a reflective section (750) is illustrated with exemplary points (754) where an optical beam may impinge on a reflective section as the reflective element rotates. The exemplary points (754) are exaggerated in FIG. 7 to help illustrate one or more embodiments of the present invention.

The reflective section (750) may be configured such that a two-dimensional pattern (e.g., two-dimensional pattern (200) shown in FIG. 2) forms a surface pattern applied to concentric rings centered about an origin (752) with lines of constant height (756). The exemplary points (754) may impinge on the reflective section (750) such that the arc formed by the exemplary points (754) does not result in a linear temporal delay. For example, the spacing between each of the exemplary points (754) is not equal when compared to the lines of constant height (756), which are equally spaced. By using a first reflective element and a second reflective element that are mirror images of each other, positioning errors for an optical beam impinging on the first reflective element may be offset by the second reflective element.

One of ordinary skill in the art, having benefit of the present invention, will understand that forming a surface pattern applied to concentric rings centered about an origin may have the origin at a location other than an axis or axial location about which a reflective element rotates.

Figure 8:
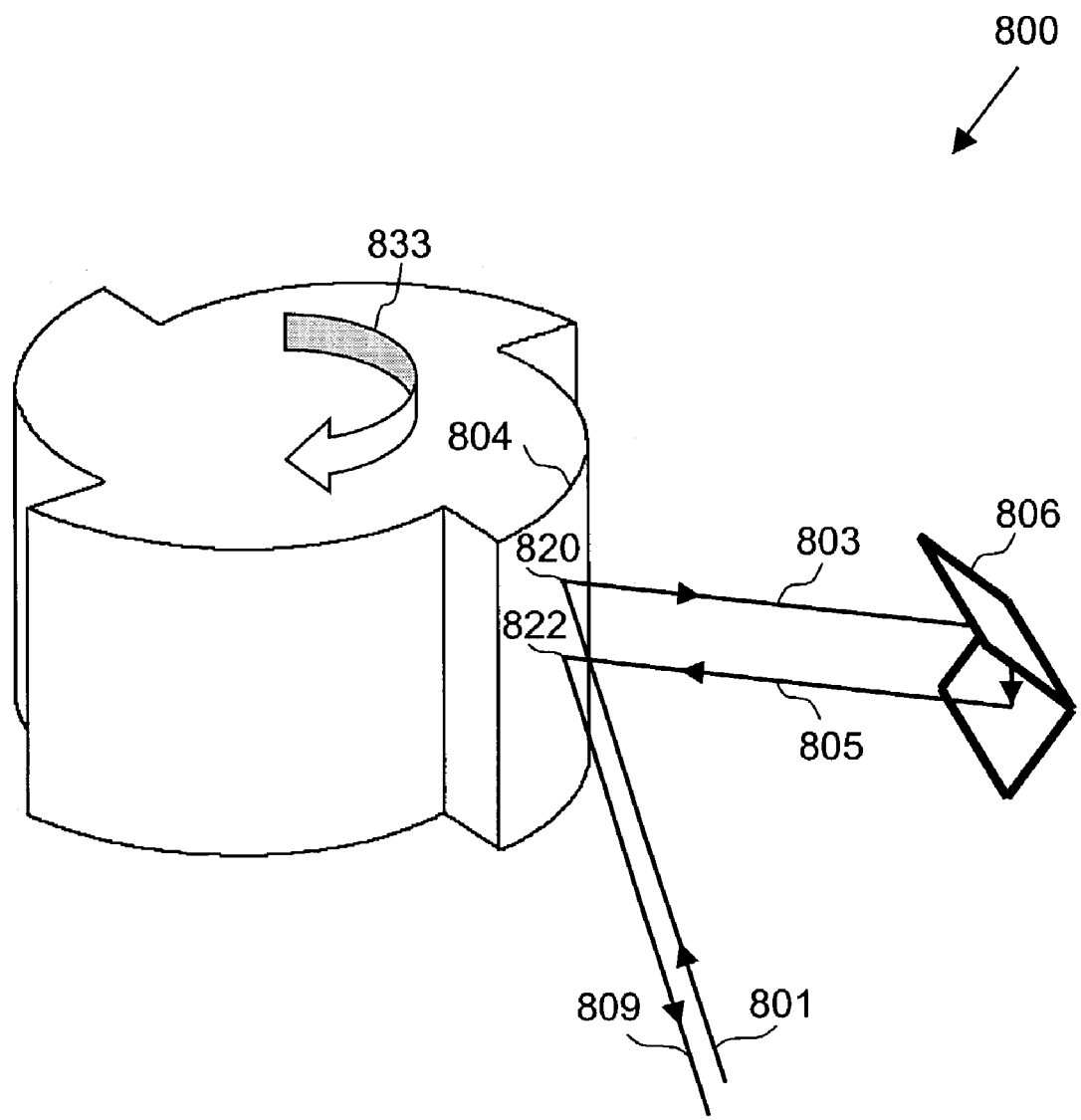
FIG. 8 shows a diagram of an optical beam path using a reflective element arranged to rotate with reflective sections with a plurality of radial distances measured from an origin in accordance with an embodiment of the present invention.

FIG. 8 shows a diagram of an exemplary optical beam path (800) using a reflective element (804) arranged to rotate with reflective sections with a plurality of radial distances measured from an origin in accordance with an embodiment of the present invention. The reflective element (804) may provide linear reflective sections that maintain a constant incidence angle between an optical input and the reflective element (804) for at least a portion of the rotation of the reflective element (804).

An optical input (801) impinges onto the reflective element (804), and an optical output (803) results from the optical input (801) reflecting off of the reflective element (804). The reflective element (804) rotates about an axis indicated by a rotation direction (833). As the reflective element (804) rotates, a constant incidence angle is maintained between the reflective element (804) and the optical input (801) for at least a portion of the rotation of the reflective element (804). Also, as the reflective element (804) rotates, a constant incidence angle is maintained between the reflective element (804) and the optical output (803) for at least a portion of the rotation of the reflective element (804). Although the constant incidence angle is maintained for at least a portion of the rotation of the reflective element (804), a point (820) at which the optical input (801) impinges on the reflective element (804) is not the same.

As the reflective element (804) rotates and the point (820) changes, the optical output (803) follows parallel paths.

Accordingly, the optical output (803) impinges at different points on a stationary retro-reflector (806) where the different points follow a straight line. In one or more embodiments, the stationary retro-reflector (806) may be a two sided (i.e., roof top or periscope) front surface reflecting, retro-reflector. The stationary retro-reflector (806) includes two flat reflecting surfaces, typically at ninety degrees to each other. Accordingly, the optical output (803) is retro-reflected along a parallel optical path to produce an optical output (805).

Because the optical output (803) moves along the stationary retro-reflector (806) in parallel paths as the reflective element (804) rotates, the optical output (805) also moves along a parallel path with respect to optical output (803). The optical output (805) may impinge on the reflective section of the reflective element (804) at a point (822) that is on the same radial line as the point (820).

An optical output (809) results from optical output (805) impinging on the reflective element (804) at the point (822). Because optical outputs (803, 805) are parallel and the constant incidence angle is maintained between the reflective element (804) and the optical outputs (803, 805) for at least a portion of the rotation of the reflective element (804), the optical output (809) is parallel to, and has a stationary optical path with respect to, optical input (801).

One of ordinary skill in the art will understand that one or more steering mirrors may be used. Accordingly, points (820, 822) may not be on the same radial line, and the optical output (809) may not be parallel with respect to optical input (801). However, optical output (809) may be stationary. Accordingly, with the addition of one or more steering mirrors, the optical output (809) may be steered parallel with respect to optical input (801).

Figure 9:
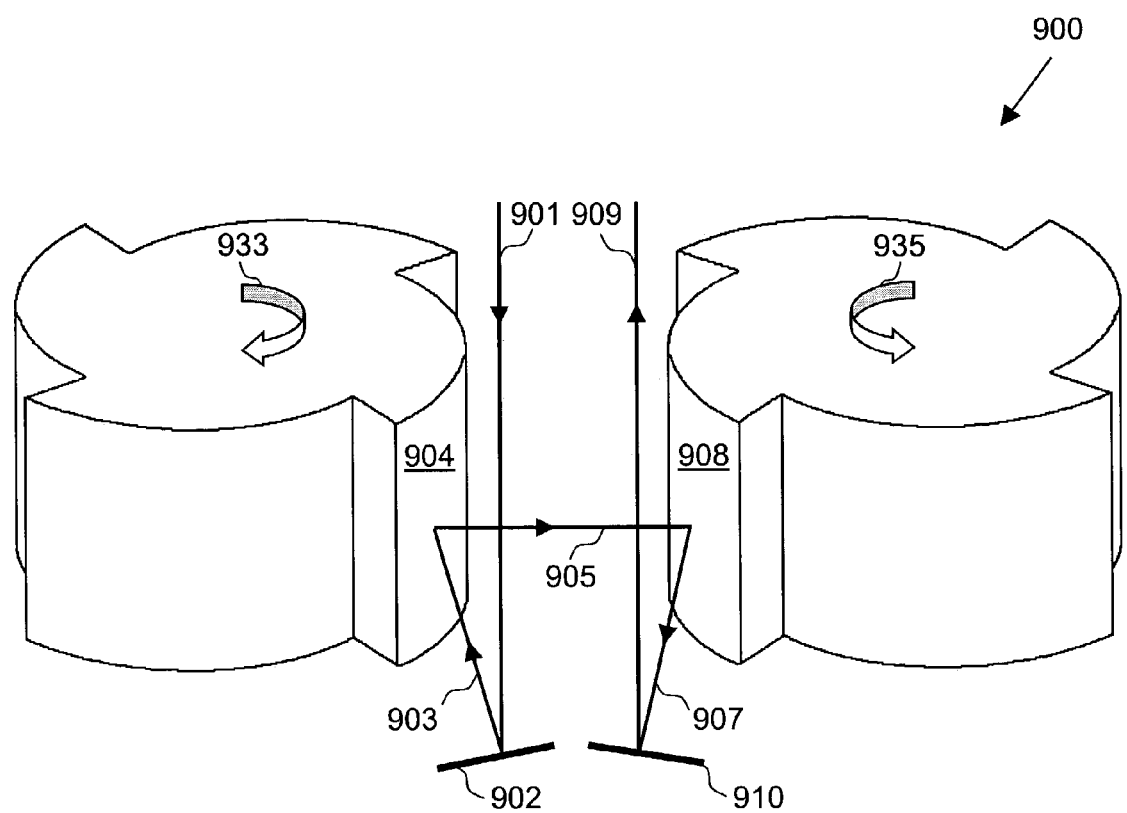
FIG. 9 shows a diagram of an optical beam path using two reflective elements arranged to rotate with reflective sections with a plurality of radial distances measured from an origin in accordance with an embodiment of the present invention.

FIG. 9 shows a diagram of an exemplary optical beam path (900) using two reflective elements arranged to rotate with reflective sections (904, 908) with a plurality of radial distances measured from an origin in accordance with an embodiment of the present invention. The two reflective elements may provide linear reflective sections (904, 908) that maintain a constant incidence angle between an optical input and the reflective elements for at least a portion of the rotation of the reflective elements.

An optical input (901) impinges onto a steering mirror (902) that steers the optical input (901) along optical path (903) onto a reflective section (904) of a first reflective element. The optical input (901) along optical path (903) impinging on the reflective section (904) of the first reflective element results in an optical output (905).

The optical output (905) impinges onto a reflective section (908) of a second reflective element. The second reflective element may be a mirror image of the first reflective element. The optical output (905) impinging on the reflective section (908) of the second reflective element results in an optical output (907). The optical output (907) impinges onto a steering mirror (910) that may steer the optical output (909) parallel to the optical input (901).

As the first reflective element rotates in a rotation direction (933) and the second reflective element rotates in a rotation direction (935), the reflective section (904) of the first reflective element and the reflective section (908) of the second reflective element move. Accordingly, the optical output (909) has an optical path length that changes. Accordingly, different temporal delays may be generated. Also, by using reflective elements with linear reflective sections, a linear temporal delay may be obtained.

By using a first reflective element and a second reflective element that are mirror images of each other, positioning errors for the optical input (901) along optical path (903) onto a reflective section (904) of the first reflective element may be offset by the second reflective element.

One of ordinary skill in the art, having benefit of the present invention, will understand that forming a surface pattern applied to a plurality of radial distances measured from an origin may have the origin at a location other than an axis or axial location about which a reflective element rotates.

One of ordinary skill in the art will understand that the steering mirror (902 and/or 910) may not be used. Accordingly, the optical input (901) may have a path similar to optical path (903). Furthermore, optical output (909) may have a path similar to optical output (907).

An input optical beam may have a stationary optical path. For a reflective element that rotates and creates a linear temporal delay for at least a portion of the rotation of the reflective element, an incidence angle between the input optical beam and the reflective element as the reflective element rotates may not change. An angle at which the output optical beam reflects from the reflective element as the reflective element rotates may not change.

One of ordinary skill in the art, having benefit of this disclosure, will understand that a two-dimensional pattern may be applied to a reflecting surface of a reflective element arranged to rotate that does not maintain a constant incidence angle between an optical input and the reflective element for at least a portion of a rotation of the reflective element. Accordingly, a secondary reflective element(s) (e.g., a stationary mirror, a stationary retro-reflecting mirror, and/or another mirror arranged to rotate) may be used to offset any variations, e.g., steering variations, caused by the reflective element. The reflective element and/or the secondary reflective element(s) may not have a linear reflective section. The combined reflective element and secondary reflective element(s) may produce a linear temporal delay.

Furthermore, a surface of the reflective element arranged to rotate may not be linear as the reflective element rotates. In other words, as the reflective element rotates, the reflective element may create an irregular temporal delay. Any collected data may have an irregular temporal spacing. The collected data with the irregular temporal spacing may be desired, or the collected data may be interpolated to create a linear temporal spacing.

In both the situations when the reflective element creates a linear temporal delay or an irregular temporal delay, an optical beam reflecting off the reflective element as the reflective element rotates has an optical path that is known. As stated above, an incidence angle (i.e., an angle between an optical beam and a line normal to a surface of a reflective element at the point where the optical beam impinges on the reflective element) determines an angle of reflection from the surface of the reflective element. The incidence angle is the same for both an input optical beam and output optical beam where the output optical beam results from the input optical beam. For a reflective element that rotates and creates an irregular (i.e., nonlinear) temporal delay, the input optical beam may have a stationary optical path; however, the incidence angle may change dependent on a shape of the reflective element. Accordingly, an angle at which the output optical beam reflects from the reflective element as the reflective element rotates may change. A secondary reflective element(s) may correct for the various optical paths of the output optical beam.

One of ordinary skill in the art, having benefit of this disclosure, will understand that a direction of rotation may be reversed for any of the embodiments of the reflective elements arranged to rotate. Reversing the direction of rotation may change whether a relatively long or short delay is encountered first.

One of ordinary skill in the art will understand that an optical output resulting from an optical input may become an optical input to a next stage of a system or reflective element (stationary or rotating). Accordingly, an optical input and an optical output should not be construed to be limited to a single stage of a system or a single reflecting element.

Figure 10:
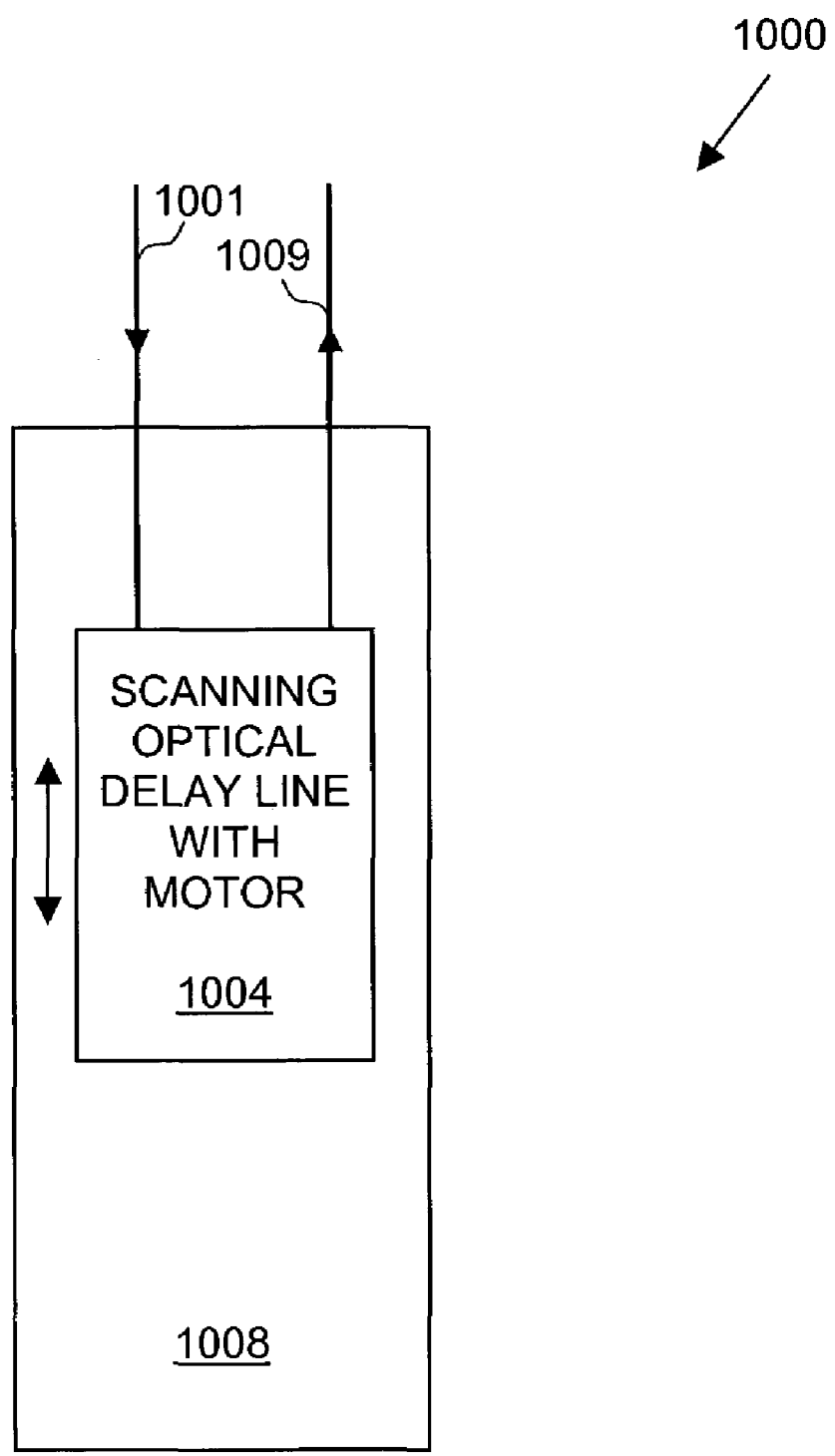
FIG. 10 shows a diagram of a scanning optical delay line with motor on a translation stage in accordance with an embodiment of the present invention.

FIG. 10 shows a diagram of an exemplary scanning optical delay line with motor on a translation stage (1000) in accordance with an embodiment of the present invention. The scanning optical delay line with motor (1004) may use at least one reflective element arranged to rotate to generate a temporal delay. The motor may be used to directly, or indirectly, rotate at least one of the at least one reflective element arranged to rotate. The scanning optical delay line with motor (1004) may receive an optical input beam (1001) and generate a temporally delayed optical output beam (1009). The optical output beam (1009) results, directly or indirectly, from the optical input beam impinging on the at least one reflective element arranged to rotate for at least a portion of a rotation of the reflective element arranged to rotate. The optical input beam (1001) and optical output beam (1009) may be parallel to each other. The scanning optical delay line with motor (1004) may have a reflective element(s) as described above.

The scanning optical delay line with motor (1004) may be mounted on a translation stage (1008). The translation stage translates the scanning optical delay line with motor (1004). Accordingly, the scanning optical delay line with motor (1004) may temporally delay the optical output beam (1009) relative to the optical input beam (1001) over a relatively small delay range. The translation stage (1008) may translate the scanning optical delay line with motor (1004) so that a longer scanning range may be obtained. Signals obtained over the relatively small delay range may be concatenated together to provide a concatenated signal with a duration having a longer scanning range.

Advantages of the present invention may include one or more of the following. In one or more embodiments, a reflective element that is arranged to rotate may have a large velocity of rotation. Accordingly, a number of temporal delay cycles available, for example, for a pump/probe experiment, may also be large. Accordingly, the present invention may have both a relatively large temporal delay and a relatively large number of temporal delay cycles.

In one or more embodiments, a linear reflective section may be created as a reflective element rotates. The linear reflective surface maintains a constant incidence angle between an optical input and the reflective element for at least a portion of a rotation of the reflective element. Accordingly, an amount of reflection of the optical input impinging on the reflective element does not vary for the at least the portion of the rotation of the reflective element.

In one or more embodiments, a linear reflective section may be created as a reflective element rotates. The linear reflective surface maintains a constant incidence angle between an optical input and the reflective element for at least a portion of a rotation of the reflective element. Accordingly, a polarization of a reflection of the optical input impinging on the reflective element does not vary for the at least the portion of the rotation of the reflective element.

In one or more embodiments, linear and/or nonlinear reflective sections may be formed on a reflective element arranged to rotate. Accordingly, linear and/or nonlinear temporal delays may be generated. Furthermore, an optical path including a linear and/or nonlinear secondary reflective element combined with the linear and/or nonlinear reflective sections formed on a reflective element arranged to rotate may produce a linear temporal delay.

In one or more embodiments, a reflective element may have a reflective front surface and/or a near front reflective surface. Accordingly, little or no dispersion may be added to an input optical beam by the reflective element.

In one or more embodiments, the present invention may produce a desired linear or nonlinear temporal delay.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus, comprising:
   a reflective element arranged to rotate about an axis,
   wherein the reflective element is configured to maintain a constant incidence angle between an optical input and the reflective element for at least a portion of a rotation of the reflective element,
   wherein the reflective element is configured to maintain a constant reflection angle between the reflective element and a first optical output for at least the portion of the rotation of the reflective element,
   wherein the reflective element is configured to change an optical delay of the first optical output relative to the optical input in response to the rotation of the reflective element,
   wherein the first optical output does not follow the same path of the optical input; and
   further comprising means for steering the first optical output back to the reflective element.

2. The apparatus of claim 1, wherein the means for steering the first optical output back to the reflective element comprises a roof top mirror.

3. The apparatus of claim 1, further comprising:
   means for rotating the reflective element.

4. The apparatus of claim 1, further comprising:
   means for translating the reflective element.

5. The apparatus of claim 1, wherein the reflective element is of a first shape comprising a reflective section with a two-dimensional pattern applied to a concentric ring centered about an origin of the first shape.

6. The apparatus of claim 1, wherein the reflective element is of a second shape comprising a reflective section with a plurality of radial distances measured from an origin of the second shape.

7. An apparatus, comprising:
   a first reflective element arranged to rotate about a first axis,
   wherein the first reflective element is configured to maintain a constant incidence angle between a first optical input and the first reflective element for at least a portion of a rotation of the first reflective element,
   wherein the first reflective element is configured to maintain a constant reflection angle between the first reflective element and a first optical output for at least the portion of the rotation of the first reflective element, wherein the first reflective element is configured to change an optical delay of the first optical output relative to the first optical input in response to the rotation of the reflective element, and wherein the first optical input does not follow a path parallel to the first axis; and a second reflective element, wherein the first optical output is incident on the second reflective element.

8. The apparatus of claim 7, further comprising:

means for rotating the first reflective element.

9. The apparatus of claim 7, wherein the first reflective element is of a first shape comprising a reflective section with a plurality of radial distances measured from an origin of the first shape.

10. The apparatus of claim 7, wherein the first reflective element is of a second shape comprising a reflective section with a two-dimensional pattern applied to a concentric ring centered about an origin of the second shape.

11. The apparatus of claim 7, wherein the second reflective element is arranged to rotate about a second axis, wherein the second reflective element is configured to maintain a constant incidence angle between a second optical input and the second reflective element for at least a portion of a rotation of the second reflective element, and wherein the second optical input is responsive to the first optical output.

12. The apparatus of claim 11, further comprising:

means for rotating the second reflective element.

13. The apparatus of claim 11, wherein the second reflective element is of a third shape comprising a reflective section with a plurality of radial distances measured from an origin of the third shape.

14. The apparatus of claim 11, wherein the second reflective element is of a fourth shape comprising a reflective section with a two-dimensional pattern applied to a concentric ring centered about an origin of the fourth shape.

15. The apparatus of claim 11, wherein the second axis is the same as the first axis.

16. The apparatus of claim 11, wherein the second reflective element is a mirror image of the first reflective element.

* * * * *